(12) United States Patent
Langella et al.

(10) Patent No.: US 10,918,678 B2
(45) Date of Patent: Feb. 16, 2021

(54) FAECALIBACTERIUM PRAUSNITZII STRAIN CNCM 1-4573 FOR THE TREATMENT AND PREVENTION OF GASTROINTESTINAL INFLAMMATION

(71) Applicants: Institut National De La Recherche Agronomique (INRA), Paris (FR); Sorbonne Universite, Paris (FR); Assistance Publique—Hopitaux de Paris, Paris (FR)

(72) Inventors: Philippe Langella, Velizy-Villacoublay (FR); Rebeca Martin Rosique, Jouy en Josas (FR); Luis Bermudez Humaran, Jouy en Josas (FR); Florian Chain, Versailles (FR); Harry Sokol, Paris (FR)

(73) Assignees: INSTITUT NATIONAL DE LA RECHERCHE AGRONOMIQUE (INRA), Paris (FR); SORBONNE UNIVERSITE, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 0 days.

(21) Appl. No.: 16/072,319

(22) PCT Filed: Jan. 23, 2017

(86) PCT No.: PCT/EP2017/051306
§ 371 (c)(1),
(2) Date: Jul. 24, 2018

(87) PCT Pub. No.: WO2017/129515
PCT Pub. Date: Aug. 3, 2017

(65) Prior Publication Data
US 2019/0030089 A1   Jan. 31, 2019

(30) Foreign Application Priority Data

Jan. 25, 2016   (FR) ..................... 16 50567

(51) Int. Cl.
| | | |
|---|---|---|
| *A01N 63/00* | (2020.01) | |
| *A61K 35/74* | (2015.01) | |
| *A23L 33/135* | (2016.01) | |
| *C12R 1/01* | (2006.01) | |
| *A61K 35/741* | (2015.01) | |
| *A61P 1/00* | (2006.01) | |

(52) U.S. Cl.
CPC ............ *A61K 35/74* (2013.01); *A23L 33/135* (2016.08); *A61K 35/741* (2013.01); *A61P 1/00* (2018.01); *C12R 1/01* (2013.01); *A23V 2002/00* (2013.01); *A23V 2200/32* (2013.01); *A23V 2200/3204* (2013.01)

(58) Field of Classification Search
CPC .................................................... A61K 35/74
See application file for complete search history.

(56) References Cited

FOREIGN PATENT DOCUMENTS

WO   WO 2016/075294   5/2016

OTHER PUBLICATIONS

Dresden (Medical News Today pp. 1-5) (www.medicalnewstoday.com/articles/323072.php (Year: 2018).*
Harvard Health Publishing (pp. 1-4) www.health.harvard.edu/a_to_z/crohns-disease-a-to-z (Year: 2018).*
Third Party Observation for application No. EP20150797929. Successful submission of observation to European Patent Office: dated Apr. 30, 2019 dated Apr. 30, 2019.
Martin et al., *The commensal Bacterium Faecalibacterium prausnitzii Is Protective in DNVS-induced Chronic Moderate and Severe Colitis Models*, 20(3) Inflamm. Bowl. Dis. 417-430 (Mar. 2014).
Martin et al., *Faecalibacterium prausnitzii prevents physiological damages in a chronic low-grade inflammation murine model*, 15(67) BMC Microbiology 1-12 (2015).
Zhang et al., *Faecalibacterium prausnitzii Inhibits Interleukin-17 to Ameliorate Colorectal Colitis in Rats*, 9(10) PLOS One 1-10 (Oct. 2014).
Langella, Commensal Bacteria and Recombinant Lactic Acid Bacteria as Novel Probiotics for Human Intestinal Health, pp. 1-61, Dec. 7, 2012, Vall d'Hebron Barcelona Hospital Institute of Research, slideshare.net, youtube.com, and web.archive.org.†

* cited by examiner
† cited by third party

*Primary Examiner* — Albert M Navarro
(74) *Attorney, Agent, or Firm* — Buchanan Ingersoll & Rooney PC

(57) ABSTRACT

The invention relates to a bacterial strain of species *Faecalibacterium prausnitzii* deposited at the CNCM under access number CNCM I-4573, for use in the treatment and/or prevention of an inflammatory gastrointestinal illness in an individual.

15 Claims, 6 Drawing Sheets

FAECALIBACTERIUM PRAUSNITZII STRAIN CNCM I-4573 FOR THE TREATMENT AND PREVENTION OF GASTROINTESTINAL INFLAMMATION

CROSS-REFERENCE TO RELATED APPLICATIONS

This application is a U.S. National Stage Application pursuant to 35 U.S.C. § 371 of International Patent Application PCT/EP2017/051306, filed on Jan. 23, 2017, and published as WO 2017/129515 on Aug. 3, 2017, which claims priority to French Patent Application 1650567, filed on Jan. 25, 2016, all of which are incorporated herein by reference in their entireties for all purposes.

FIELD OF THE INVENTION

The present invention relates to a *Faecalibacterium prausnitzii* strain for use thereof in the treatment and prevention of inflammatory gastrointestinal diseases (IBD) in an individual, in particular inflammatory bowel diseases (IBD).

PRIOR ART

Inflammation is a natural biological process which constitutes a normal part of the response to lesions or infections and contributes to protecting the organism against internal or external attacks.

However, a dysfunction of the inflammation mechanisms, in particular a persistent or excessively abundant inflammation, may cause painful diseases and endanger the patient's life. Such diseases comprise, for example, skin disorders, bowel disorders, neurological disorders, arthritis and autoimmune diseases. Several of these inflammatory diseases still have no treatment or have no appropriate treatment.

Consequently, the study of and search for new anti-inflammatory treatment strategies constitutes a major subject in medicine and in biomedical research.

An inflammatory bowel disease is a group of disorders characterized by a chronic and recurrent inflammation of the gastrointestinal tract. The most common form of this group is Crohn's disease. The pathogenesis involves inappropriate and continuous activation of the mucosal immune system caused by the presence of the intestinal microbiota in a genetically predisposed patient.

There is a constant need for novel substances, in particular probiotics, or compositions for the treatment and/or prevention of inflammatory gastrointestinal diseases, in particular inflammatory bowel diseases, in an individual.

SUMMARY OF THE INVENTION

The objective of the present invention is to describe novel substances, in particular probiotics, and compositions for the treatment and/or prevention of inflammatory gastrointestinal diseases in an individual, in particular inflammatory bowel diseases in an individual.

In the context of the present invention, the term "prevent" denotes the reduction to a lesser degree of the risk or of the probability of occurrence of a given phenomenon, that is to say, in the present invention, a gastrointestinal inflammation, in particular a bowel inflammation.

The present invention is based on the discovery, by the present inventors, of the anti-inflammatory properties of the *Faecalibacterium prausnitzii* strain deposited with the CNCM under accession number CNCM I-4573.

According to the experimental results of the inventors, a specific strain of *Faecalibacterium prausnitzii* (*F. preintsnitzii*), deposited with the Collection Nationale de Cultures de Microorganisines ("CNCM") at Institut Pasteur, 25 rue de Docteur Roux, F-75724 Paris Cedex 15, France on Dec. 7, 2011, under accession number CNCM I-4573, has the unexpected capacity to reduce, in vitro and in vivo, a gastrointestinal inflammation, in particular a bowel inflammation, in an individual. As illustrated in the examples and described hereinafter, the inventors have demonstrated that, on the other hand, the *F. prausnitzii* strain 1-4575 does not possess such advantageous properties.

The strain according to the invention is more particularly capable of reducing the production of pro-inflammatory molecules, such as interleukin 8 (IL-8), interleukin 2 (IL-2), interleukin 4 (IL-4), interleukin 6 (IL-6) and gamma-interferon (INFγ), and increasing the production of anti-inflammatory molecules, such as interleukin 10 (IL-10).

According to a first subject, the present invention relates to a bacterial strain of the species *Faecalibacterium prausnitzii* deposited with the CNCM under the accession number CNCM I-4573, for use thereof in the treatment and/or prevention of an inflammatory gastrointestinal disease in an individual, in particular of an inflammatory bowel disease in an individual, more particularly of a colonic inflammatory bowel disease in an individual.

This strain identified by the inventors is therefore a probiotic strain which may be used for the applications indicated above.

An individual according to the invention is preferably a mammal, including a non-human mammal, and is, in particular, a human being.

The inflammatory gastrointestinal disease is, in particular, an inflammatory bowel disease (IBD), more particularly a colonic inflammatory bowel disease.

Said colonic inflammatory bowel disease may, in particular, be chosen from the group consisting of Crohn's disease, ulcerative colitis and pouchitis, in particular Crohn's disease and ulcerative colitis.

According to another embodiment, the bacterial strain for use thereof according to the invention is included in a composition comprising a physiologically acceptable medium, preferably in an oral composition, and more particularly preferably in a food supplement.

The term "physiologically acceptable medium" is intended to denote a medium which is compatible with the body of the individual to whom said composition must be administered. It is, for example, a non-toxic solvent such as water. In particular, said medium is compatible with oral administration.

A composition of the invention is preferably for oral administration.

A composition of the invention for oral administration may be chosen from the group consisting of a food product, a beverage, a pharmaceutical product, a nutraceutical, a food additive, a food supplement and a milk product and is, in particular, in the form of a food supplement

FIGURE LEGENDS

FIG. 1 illustrates the concentration of interleukin 8 (IL-8) (in pg of IL-8/mg of proteins) in Ht-29 cells stimulated with TNFα: (a) only in YBHI medium (control); (b) treated with the *F. prausnitzii* strain A2-165; (c) treated with the *F. prausnitzii* strain I-4573 according to the invention; or (d)

treated with the *F. prausnitzii* strain I-4575. The tests are carried out in triplicate. The results are standardized using, as reference value, IL-8 produced after co-induction with PBS as negative control. *p<0.05.

FIG. 6 illustrates the concentrations of colonic cytokines ((FIG. 6A) IL-2, (FIG. 6B) IL-4, (FIG. 6C) IL-6 and (FIG. 6D) IFNg) (in pg/ml) (a) of control mice (without colitis) receiving only EtOH; (b) of control mice having a DNBS colitis and treated with PBS; (c) of mice having DNBS colitis and treated with the *F. prausnitzii* strain A2-165; (d) of mice having a DNBS colitis and treated with the *F. prausnitzii* strain I-4573; and (e) of mice having a DNBS colitis and treated with the *F. prausnitzii* strain I-4575.

DETAILED DESCRIPTION OF THE INVENTION

The present inventors have carried out thorough studies in order to identify the capacity of a specific strain of *Faecalibacterium prausnitzii* to treat and/or prevent inflammatory gastrointestinal diseases in an individual, in particular inflammatory bowel diseases in an individual.

Indeed, the inventors have determined, unexpectedly, that the *F. prausnitzii* strain I-4573 has the capacity to reduce a gastrointestinal inflammation, in particular a bowel inflammation, in an individual.

It is presently described that the bacterial strain of the invention may, in particular, reduce the concentration of pro-inflammatory molecules, such as interleukin 8 (IL-8), interleukin 2 (IL-2), interleukin 4 (IL-4) and interleukin 6 (IL-6).

It is also presently demonstrated that the bacterial strain of the invention is, in particular, capable of increasing the concentration of anti-inflammatory molecules, such as interleukin 10 (IL-10).

*Faecalibacterium Prausnitzii* Strain of the Invention

*F. prausnitzii* is a major member of the phylum Firmicutes and is part of the commensal bacteria that are the most abundant in the microbiota of the healthy human large intestine.

*F. prausnitzii* is an extremely oxygen-sensitive (EOS) bacterium which is therefore difficult to culture, even under anaerobic conditions (Duncan et al. 2002, Int. J. Syst. Evol. Microbiol. 52(Pt 6): 2141-6 and Lopez-Siles et al. Appl. Environ Microbiol. January 2012; 78 (2):420-8). *F. prausnitzii* is, in particular, known to be one of the most abundant butyrate-producing bacteria in the human digestive tract, the butyrate short-chain fatty acid being very important in intestinal physiology, systemic functions and beneficial effects on human health (Macfarlane and Macfarlane (2011), J. Clin. Gastroenterol. 45 Suppl: S120-7).

The *F. prausnitzii* strain A2-165 is also known to have anti-inflammatory and protective effects in murine models of acute and chronic colitis, that is to say in inflammatory disorders (Martin et al., Inflamm Bowel Dis. March 2014; 20(3):417-30 and Sokol et al., Proc Natl Acad Sci USA. Oct. 28, 2008; 105(43):16731-6).

The anti-inflammatory properties of the A2-165 strain cannot generally be attributed to the *F. prausnitz* species, given that the existence of anti-inflammatory properties is unpredictable for a given strain of *F. prausnitzii*. Indeed, such a specific anti-inflammatory activity is illustrated in the examples, in which a comparative test was carried out with an *F. prausnitzii* strain not part of the invention, namely the CNCM I-4575 strain, which does not have the anti-inflammatory activity of the strain of the invention.

A suitable daily dose of a bacterial strain according to the invention is from $10^7$ to $10^{11}$ colony-forming units (cfu) as a medicament, for example in the form of a daily dose equivalent to $10^9$ cfu.

A *Faecalibacterium prausnitzii* strain of the invention is for use thereof in the treatment and/or prevention of a gastrointestinal inflammation in an individual, in particular of a bowel inflammation in an individual.

The strain of the invention is a probiotic, the activity of which is located in the intestines. A probiotic bacterium according to the invention denotes a bacterium which, when it is ingested live in sufficient amounts, may exert beneficial effects on human health.

Consequently, this strain must be administered live in the intestines.

The bacterial strain of the invention may be administered to the intestines of an individual to be treated in various ways, namely orally or rectally. A bacterium according to the invention is preferably administered orally.

According to one preferred embodiment, the bacterial strain of the invention is included in a composition comprising a physiologically acceptable medium. Such a composition is preferably for oral administration, and in particular in the form of a food supplement.

Compositions

The present invention also relates to a composition comprising, in a physiologically acceptable medium, at least the *Faecalibacterium prausnitzii* bacterial strain I-4573 of the invention.

A composition according to the invention is intended for the digestive tract, in particular the intestines.

Consequently, a composition according to the invention is chosen from an oral or rectal composition. A composition of the invention is preferably an oral or rectal composition, more preferably an oral composition.

According to one embodiment, a composition of the invention is an oral composition, that is to say that it is intended for oral administration to a subject.

Such a composition may be in the form of a suspension, a tablet, a pill, a capsule, a granule or a powder.

The composition according to the invention for oral administration may be chosen from the group consisting of a food product, a beverage, a pharmaceutical product, a nutraceutical, a food additive, a food supplement or a milk product and is, in particular, a food supplement.

According to one preferred embodiment, a composition according to the invention is a food supplement.

A food supplement for oral administration may be present in capsules, gel capsules, soft capsules, tablets, sugar-coated tablets, pills, pastes, lozenges, gums, oral solutions or emulsions, a syrup or a gel.

Advantageously, a composition according to the invention, intended for oral administration, may be provided with a gastric-juice-resistant coating, in order to ensure that the bacterial strain of the invention included in said composition can pass through the damaged stomach. The release of the bacterial strain may thus take place for the first time in the upper intestinal tract.

A food supplement according to the invention may also comprise a sweetener, a stabilizer, an antioxidant, an additive, a flavoring agent and/or a dye.

The formulation thereof is carried out by means of the usual methods for producing sugar-coated tablets, gel capsules, gels, controlled-release hydrogels, emulsions, tablets or capsules.

A composition according to the invention may also be in the form of a nutritional composition.

A nutritional composition according to the invention is in the form of a yogurt, a cereal bar, breakfast cereals, a dessert, a frozen food, a soup, a pet food, a liquid suspension, a powder, a tablet, a gum or a candy.

In another embodiment of the invention, a composition containing the bacterial strain of the invention is administered intrarectally.

Preferably, a rectal administration is carried out in the form of a suppository, an enema or a foam.

In particular, a composition of the invention is suitable for the administration of a daily dose representing from $10^7$ to $10^{11}$ colony-forming units (cfu) as a medicament, preferably a daily dose equivalent to $10^9$ cfu.

For example, a composition according to the invention may be administered to an individual requiring it, at a single daily dose of 1 g containing the I-4573 bacterial strain of the invention in an amount equivalent to a dose of between $10^7$ and $10^{11}$ cfu, preferably $10^9$ cfu.

In another example, a composition according to the invention may be administered to an individual requiring it, at a single daily dose of 0.2 g containing the I-4573 bacterial strain of the invention in an amount equivalent to an amount of between $10^7$ and $10^{11}$ cfu, preferably $10^9$ cfu.

In another example, a composition according to the invention may be administered to an individual requiring it, twice a day on the basis of two doses of 1 g, each dose containing, independently, the I-4573 bacterial strain of the invention in an amount equivalent to an amount of between $5\times10^6$ and $5\times10^{10}$ cfu (on the dry weight basis), preferably $5\times10^8$ cfu, so that the total daily dose of the I-4573 bacterial strain of the invention administered to the individual is as indicated above.

A composition according to the invention may also comprise at least one among: antioxidants, fish oils, DHA, EPA, vitamins, minerals, phytonutrients, a protein, a lipid, probiotics, and combinations thereof.

The invention is described below in greater detail by means of the following examples which are given solely by way of illustration.

All the references to percentages are percentages by weight unless otherwise indicated.

EXAMPLES

The *F. prausnitzii* strain according to the invention, deposited with the CNCM under the accession number CNCM I-4573, was tested and compared to two other *F. prausnitzii* strains, A2-165 and CNCM I-4575, for its capacity to modulate, in vitro and in vivo, the immune response and have a direct impact on bowel inflammation.

In the in vitro tests, two different cell models are used: HT-29 and PBMC.

In the in vivo tests, a murine colitis model is used.

In Vitro Tests

I. Bacterial Strains and Culture Conditions

The isolates of the *F. prausnitzii* strains tested are cultured in YBHI medium (brain-heart perfusion medium supplemented with 0.5% of yeast extract) (Difco, Detroit, United States) supplemented with 1 mg/ml of cellobiose (Sigma-Aldrich Chemie Gmbh, Buchs, Switzerland), 1 mg/ml of maltose (Sigma-Aldrich) and 0.5 mg/ml of cysteine (Sigma-Aldrich) at 37° C. in an anaerobic chamber filled with $N_2$=85%, $CO_2$=10% and $H_2$=5%.

The strains are isolated from healthy patients:
CNCM-I4573 and CNCM-I4575 strains from a 40-year-old man; and
A2-165 (DSMZ 17677) strain from a 34-year-old woman from Duncan S H et al. IJSEM, 2002, 52(Pt 6):2141-2146.

II. Immunomodulatory Properties by Means of HT-29 Cells

A. Cell Culture

The HT-29 cell line (ATCC HTB-38) (LGC-Standars) is cultured in Dulbecco's minimum essential Modified Eagle Medium (DMEM) (Sigma-Aldrich) supplemented with 10% (w/v) of heat-inactivated fetal bovine serum (FBS) (Gibco-BRL, Eragny, France) and with penicillin G/streptomycin (5 000 IU/ml, 5 000 µg/ml) (Sigma-Aldrich). The cultures are incubated in 25 cm² tissue culture flasks (Nunc, Roskilde, Denmark) at 37° C. in an atmosphere containing 5% (v/v) $CO_2$ until confluency.

B. Anti-Inflammatory Tests

Anti-inflammatory tests using HT-29 are carried out according to the procedure described by Kechaou et al. (Applied and environmental microbiology 2012, 79(5): 1491-1499).

Briefly, 50 000 HT-29 cells per well are seeded in 24-well culture plates (Nunc). Twenty-four hours before bacterial stimulation, the culture medium is replaced by a medium with 5% FBS.

The tests begin on day 7 after seeding, when the cells are at confluency ($1.83\times10^6$ cells/well). Twenty-four hours before the bacterial coculture (day 6), the culture medium is replaced by a medium with 5% heat-inactivated FBS and 1% glutamine.

On the day of the coculture, 10% of bacterial supernatant is added in DMEM in a total volume of 500 µl. The cells are simultaneously stimulated with human TNF-α (5 ng/ml; Peprotech, NJ) for 6 h at 37° C. in 10% $CO_2$.

All the samples are analyzed in triplicate.

After co-incubation, the cell supernatants are collected and stored at −80° C. until subsequent analysis of the concentrations of interleukin 8 (IL-8) by ELISA (Biolegend, San Diego, Calif.).

The total proteins are determined by means of the Bradford reagent test (Sigma-Aldrich). The tests are carried out at least in triplicate.

The results are expressed as IL-8/protein (pg/mg) and are standardized using, as reference value, IL-8 produced after the co-incubation with PBS as negative control.

C. Statistical Analysis

The statistical analysis is carried out by means of the GraphPad software (GraphPad Software, La Jolla, Calif., United States). All the data are expressed in the form of mean +/−SEM.

The comparisons are carried out with the non-parametric Kruskal-Wallis test followed by a Dunn's multiple comparison test.

The correlation tests are carried out by means of the Spearman test.

A value p of less than 0.05 is considered to be significant.

D. Results

Figure 1:
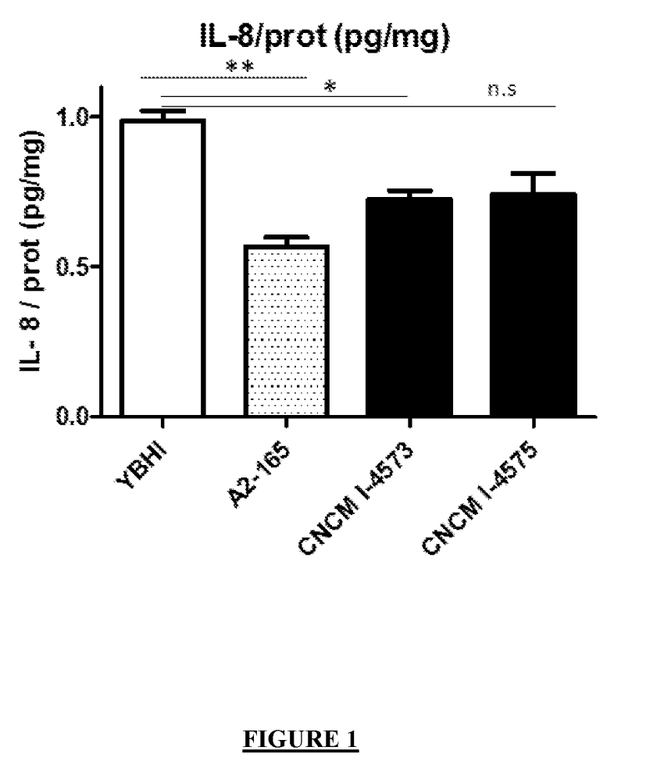

The results obtained are presented in FIG. 1.

It may be observed from these tests that the CNCM I-4573 strain is capable of significantly reducing the production of pro-inflammatory cytokine IL-8 induced by the stimulation of TNF-α in HT-29 epithelial cells.

As anticipated, the *F. prausnitzii* strain A2-165 also produces such a reduction in IL-8 production.

Conversely, the *F. prausnitzii* strain I-4575 does not induce a statistically significant decrease in IL-8.

III. Immunomodulatory Properties by Means of PBMCs

A. Cell Culture

Commercial PBMCs (StemCell Technologies, France) from five healthy donors are used.

The donors have the following characteristics: men, less than 65 years old, body mass index<30, non-smoker, no medicaments having known anti-inflammatory effects taken during the 15 days preceding the selection, and negative test for HIV, hepatitis A and hepatitis B viruses.

After reception, the cells are stored in liquid nitrogen until use.

B. Anti-Inflammatory Tests

In order to prepare PBMCs for coculture tests with *F. prausnitzii* bacteria, the flasks are thawed at 37° C. in a water bath and then transferred into a medium containing RPMI-1640 medium supplemented with 10% heat-inactivated FCS, 1% L-glutamine and 0.1% penicillin/streptavidin (the components of the medium are purchased from Lonza, Switzerland). DNase (100 µg/ml, Roche Applied Science, France) is added to the medium in order to prevent cell agglomeration.

The cells are then centrifuged at 200 g for 15 min, counted using trypan blue and plated out on 24-well plates at $1\times10^6$ cells/well. Supernatants are added in triplicate (three wells per donor) at 10% in a total volume of 1 ml. The plates are incubated for 24 h at 37° C. with 10% $CO_2$.

The culture supernatants are collected, mixed with a cocktail of anti proteases in accordance with the manufacturer's instructions (EDTA-complete protease inhibitor, Roche Applied Bioscience) and stored at −80° C. until subsequent analysis of the interleukin 10 (IL-10) concentrations by ELISA (Mabtech, Sweden).

C. Statistical Analysis

The statistical analysis is carried out by means of the GraphPad software (GraphPad Software, La Jolla, Calif., United States). All the data are expressed in the form of mean +/−SEM.

The comparisons are carried out with the non-parametric Kruskal-Wallis test followed by a Dunn's multiple comparison test.

The correlation tests are carried out by means of the Spearman test.

A value p of less than 0.05 is considered to be significant.

D. Results

Figure 2:
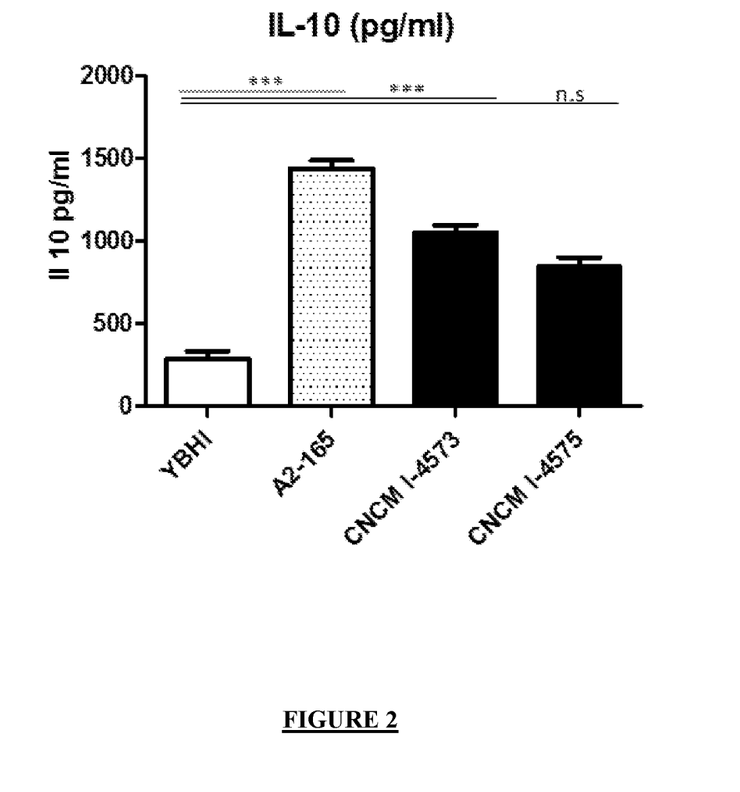
FIG. 2 illustrates the concentration of interleukin 10 (IL-10) (in pg of IL-10/ml of proteins) in peripheral blood mononuclear cells (PBMCs): (a) only in YBHI medium (control); (b) treated with the *F. prausnitzii* strain A2-165; (c) treated with the *F. prausnitzii* strain I-4573 according to the invention; or (d) treated with the *F. prausnitzii* strain I-4575. The tests are carried out in triplicate. ***p<0.001.

The results obtained are presented in FIG. 2.

These tests demonstrate that the CNCM I-4573 strain is capable of significantly increasing the production of anti-inflammatory cytokine IL-10 in PBMCs.

As anticipated, the *F. prausnitzii* strain A2-165 also produces such an increase in IL-10 production.

Conversely, the *F. prausnitzii* strain I-4575 does not induce a statistically significant increase in IL-10.

In Vivo Tests

A. Induction of DNBS Colitis and Administration of Bacteria

The DNBS-induced colitis protocol is as previously described (Martin R, et al. Inflamm Bowel Dis. March 2014; 20(3):417-30).

Briefly, the mice are anesthetized with enflurane (Abbott, Abbott Park, Ill.) and a segment 10 cm long of PE-90 tubing (ClayAdam, Parsippany, N.J.) is attached to a syringe of tuberculin and inserted 3.5 cm into the colon.

The colitis is induced by intrarectal (i.r.) injection by means of this tube of 200 mg/kg of DiNitroBenzene-Sulfonic acid (DNBS) (ICN, Biomedical Inc.) solution in ethanol at 30% (EtOH).

The control mice (without colitis) receive only EtOH.

Figure 3:
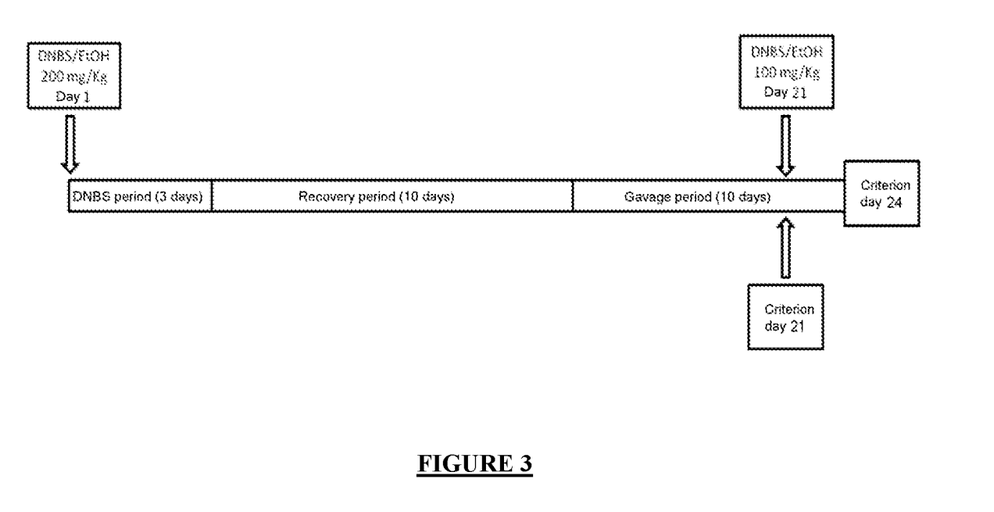
FIG. 3 illustrates the experimental protocol for the chronic colitis model in mice (DNBS).

The mice are fed with 6% sucrose in the drinking water for the first three days after the DNBS injection in order to prevent dehydration (DNBS period). 10 days after the DNBS period, 200 µl containing $1\times10^9$ CFU of one of the bacterial strains are administered intragastrically, each day for 10 days (gavage period) (see FIG. 3).

The study groups are as follows: non-colitis control group (EtOH+PBS), colitis control group (DNBS+PBS), group of *F. prausnitzii* strain A2-165 (DNBS+A2-165), *F. prausnitzii* strain CNCM-I4573 (DNBS+CNCM-I4573) and *F. prausnitzii* strain CNCM-I4575 (DNBS+CNCM-I4575).

The colitis is reactivated 21 days after the first injection of DNBS (recovery period) with a second injection of 100 mg/kg of DNBS solution.

The seriousness of the colitis is then determined by monitoring the weight loss (results not presented) for the 3 days following the second injection.

B. Macroscopic Scores

The mice are sacrificed by cervical dislocation and the abdominal cavity is opened. The colon and the small intestine are removed and opened longitudinally; the macroscopic damage is immediately evaluated.

The macroscopic scores are recorded by means of a system previously described for DNBS colitis.

Briefly, the macroscopic criteria (evaluated on a scale of 0 to 9) comprise macroscopic damage of the mucosae (such as ulcers, thickening of the colonic wall, presence of adhesions between the colon and other intra-abdominal organs), consistency of fecal matter (as an indicator of diarrhea) and the presence of hyperemia.

Figure 4:
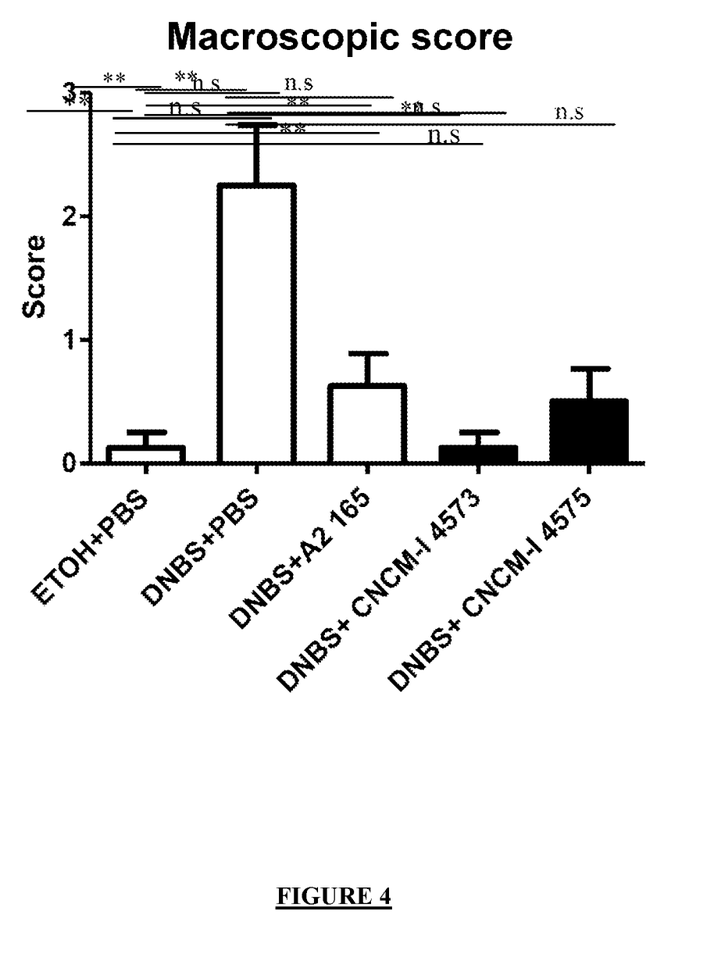
FIG. 4 illustrates the macroscopic scores of the colon and of the small intestine (a) of control mice (without colitis) receiving only EtOH; (b) of control mice having a DNBS colitis and treated with PBS; (c) of mice having a DNBS colitis and treated with the *F. prausnitzii* strain A2-165; (d) of mice having a DNBS colitis and treated with the *F. prausnitzii* strain I-4573; and (e) of mice having a DNBS colitis and treated with the *F. prausnitzii* strain I-4575. The macroscopic criteria (evaluated on a scale of 0 (no damage) to 9) comprise macroscopic damage of the mucosae (such as ulcers, thickening of the colonic wall, presence of adhesions between the colon and other intra-abdominal organs), consistency of fecal matter (as an indicator of diarrhea) and the presence of hyperemia. n=8. **p<0.01.

The results obtained are represented in FIG. 4.

C. Myeloperoxidase (MPO) Activity

The myeloperoxidase (MPO) activity, used as neutrophil infiltration marker, is assayed using a modified version of the method described by Bradley et al. (J. Invest. Dermatol. 1982, 78(3):206-209).

A one-centimeter length of distal colon is recovered and homogenized (50 mg/ml) in ice-cold 50 mM potassium phosphate buffer (pH 6) containing 5% of hexadecyltrimethylammonium bromide (Sigma-Aldrich) and hydrogen peroxide ($H_2O_2$).

The colorimetric reaction is monitored by measuring the absorbance with a spectrophotometer.

Figure 5:
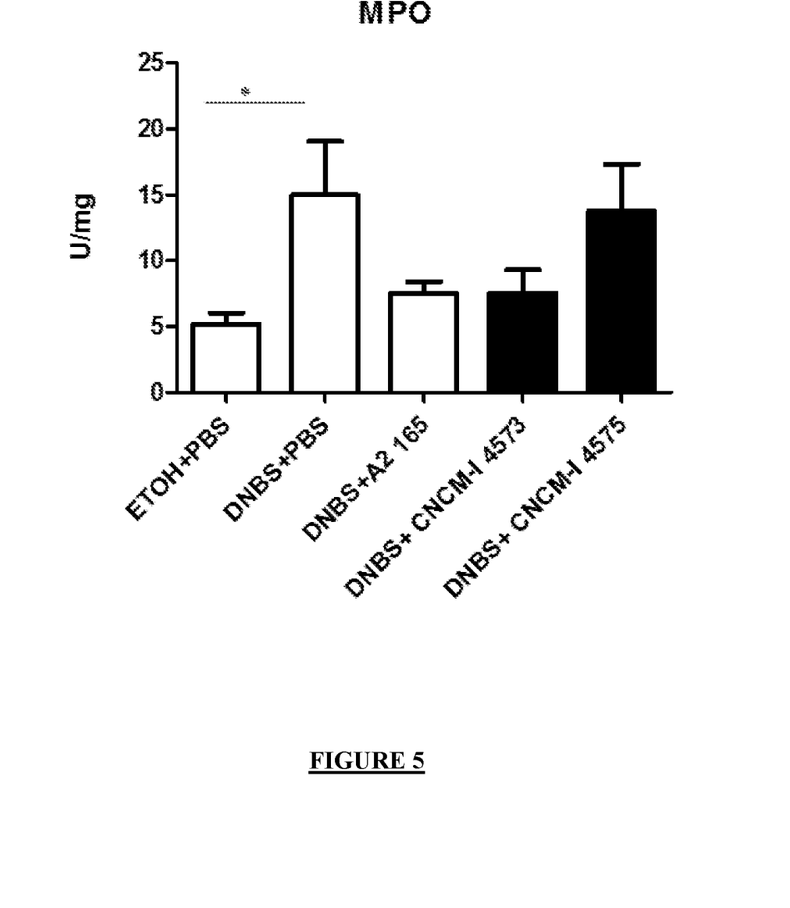
FIG. 5 illustrates the myeloperoxidase (MPO) activity (U/mg) in the distal colon (a) of control mice (without colitis) receiving only EtOH; (b) of control mice having a DNBS colitis and treated with PBS; (c) of mice having a DNBS colitis and treated with the *F. prausnitzii* strain A2-165; (d) of mice having a DNBS colitis and treated with the *F. prausnitzii* strain I-4573; and (e) of mice having a DNBS colitis and treated with the *F. prausnitzii* strain I-4575. n=8. *p<0.05.

The results obtained are represented in FIG. 5.

D. Cytokine Assays

A one-centimeter length of distal colon is recovered and homogenized in 400 µl of Tris-HCl buffer containing protease inhibitors (Sigma-Aldrich) in a tissue lyser.

The samples are centrifuged for 20 min and the supernatant is frozen at −80° C. until subsequent analysis.

Before the sacrifice, the blood samples are obtained from the retro-orbital venous plexus and centrifuged, then the serums are stored at −80° C. until analysis.

The pro-inflammatory cytokines (IL-6, IL-4, IFN-γ, and IL-2) are assayed at least from a cytometric bead array system (BD, NJ, United States).

The results obtained are presented in FIGS. 6a (IL-2), 6b (IL-4), 6c (IFN-γ) and 6d (IL-6).

E. Statistical Analysis

The GraphPad software (GraphPad Software, La Jolla, Calif., United States) is used for the statistical analysis.

The results are presented in the form of bar graphs +/−SEM.

The comparisons are carried out with the non-parametric Kruskal-Wallis test followed by a Dunn's multiple comparison test. The correlation tests are carried out by means of the Spearman test.

A value p of less than 0.05 is considered to be significant.

F. Results

1. The macroscopic scores of FIG. 4 show that a very good score is obtained in DNBS mice treated with the I-4573 strain, equivalent to that obtained in the control mice not having colitis.

Conversely, the scores obtained with DNBS mice treated with the A2-165 strain or the I-4575 strain are higher on the scale of macroscopic criteria than those obtained with the control mice not having colitis and the DNBS mice treated with the I-4573 strain.

2. With regard to the myeloperoxidase activities measured, the activities obtained with DNBS mice treated with the I-4573 strain or with the A2-165 strain are virtually similar to the activity obtained with the control mice not having colitis.

Conversely, the activity obtained with DNBS mice treated with the I-4575 strain is similar to the activity obtained with non-treated control DBNS mice.

3. Finally, the pro-inflammatory cytokine profile obtained with DNBS mice treated with the I-4573 strain and DNBS mice treated with the A2-165 strain clearly demonstrates the anti-inflammatory effect of these two strains.

In fact, with regard in particular to the DNBS mice treated with the I-4573 strain, the IL-2 and IL-4 expression levels are similar to those obtained with control mice not having colitis. The IFN-γ and IL-6 expression levels are more reduced compared to those obtained with the non-treated control DNBS mice.

Conversely, the I-4575 strain shows no anti-inflammatory property. The IL-2, IL-4, IL-6 and IFN-γ expression levels thereof are similar to, or even greater than, those observed with the non-treated control DNBS mice.

Consequently, it is demonstrated in the present examples that the *F. prausnitzii* strain I-7573 advantageously has anti-inflammatory properties and that not all the *F. prausnitzii* strains have such properties, as demonstrated with the I-4575 strain.

The invention claimed is:

1. Method for the treatment of an inflammatory gastrointestinal disease in an individual comprising administering to the said individual a bacterial strain of the species *Faecalibacterium prausnitzii* deposited with the CNCM under accession number CNCM 1-4573.

2. The method as claimed in claim 1, characterized in that the individual is a mammal.

3. The method as claimed in claim 1, characterized in that the individual is a human being.

4. The method as claimed in claim 1, characterized in that the inflammatory gastrointestinal disease is an inflammatory bowel disease.

5. The method as claimed in claim 1, characterized in that the inflammatory gastrointestinal disease is a colonic inflammatory bowel disease.

6. The method as claimed in claim 5, characterized in that the colonic inflammatory bowel disease is chosen from the group consisting of Crohn's disease, ulcerative colitis and pouchitis.

7. The method as claimed in claim 5, characterized in that the colonic inflammatory bowel disease is chosen from the group consisting of Crohn's disease and ulcerative colitis.

8. The method as claimed in claim 1, characterized in that the bacterial strain is included in a composition comprising a physiologically acceptable medium.

9. The method as claimed in claim 1, characterized in that the bacterial strain is included in an oral composition.

10. The method as claimed in claim 1, characterized in that the bacterial strain is included in a food supplement.

11. The method as claimed in claim 8, characterized in that the composition is suitable for the administration of a daily dose representing from $10^7$ to $10^{11}$ colony-forming units (cfu) as a medicament.

12. The method as claimed in claim 8, characterized in that the composition is for oral administration and is chosen from the group consisting of a food product, a beverage, a pharmaceutical product, a nutraceutical, a food additive, a food supplement and a milk product.

13. The method as claimed in claim 12, characterized in that the composition is for oral administration and is a food supplement.

14. The method as claimed in claim 9, characterized in that the composition is suitable for the administration of a daily dose representing from $10^7$ to $10^{11}$ colony-forming units (cfu) as a medicament.

15. The method as claimed in claim 10, characterized in that the composition is suitable for the administration of a daily dose representing from $10^7$ to $10^{11}$ colony-forming units (cfu) as a medicament.

* * * * *